United States Patent
Jung et al.

(10) Patent No.: US 6,309,790 B1
(45) Date of Patent: Oct. 30, 2001

(54) ORGANIC ANTI-REFLECTIVE COATING MATERIAL AND ITS PREPARATION

(75) Inventors: Min-Ho Jung; Sung-Eun Hong; Ki-Ho Baik, all of Gyunggi-do (KR)

(73) Assignee: Hyundai Electronics Industries Co., Ltd. (KR)

( * ) Notice: Subject to any disclaimer, the term of this patent is extended or adjusted under 35 U.S.C. 154(b) by 0 days.

(21) Appl. No.: 09/499,873

(22) Filed: Feb. 7, 2000

(30) Foreign Application Priority Data

Mar. 15, 1999 (KR) .................................................. 99-8668

(51) Int. Cl.$^7$ .............................. G03F 7/004; C08F 18/16

(52) U.S. Cl. ..................................... 430/270.1; 430/271.1; 430/910; 526/273; 526/326; 526/329.7

(58) Field of Search .............................. 430/270.1, 271.1; 526/320, 326, 329.7, 273

(56) References Cited

U.S. PATENT DOCUMENTS

| | | | |
|---|---|---|---|
| 4,413,052 | * 11/1983 | Green et al. | 430/327 |
| 5,677,112 | * 10/1997 | Urano et al. | 430/325 |

FOREIGN PATENT DOCUMENTS

916683 * 5/1999 (EP) .

OTHER PUBLICATIONS

Holden, D.A., et al. Macromolecules, 1980, 13, 289–295.*
March, J., Advanced Organic Chemistry, McGraw–Hill, 2nd ed., New York, 1977, pp. 361–362.*

* cited by examiner

*Primary Examiner*—Rosemary Ashton
(74) *Attorney, Agent, or Firm*—Townsend and Townsend and Crew LLP

(57) ABSTRACT

Polymers are provided having the following formulas I and II:

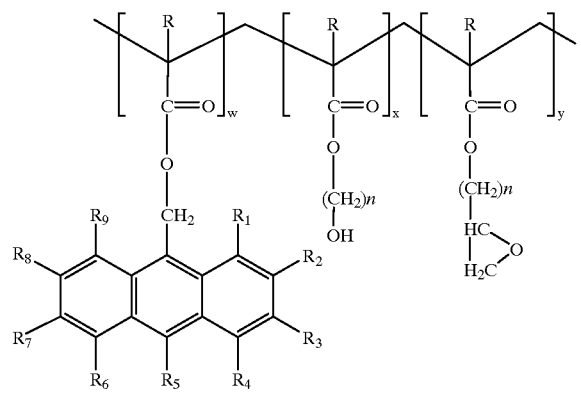

(general formula I)

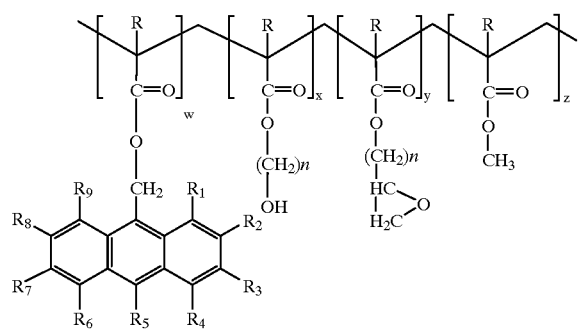

(general formula II)

Polymers of the present invention can be used to provide an anti-reflective coating (ARC) material useful for submicrolithography processes using 248 nm KrF, 193 nm ArF and 157 nm $F_2$ lasers. The polymers contain chromophore substituents which exhibit sufficient absorbance at wavelengths useful for such submicrolithography process. The ARC prevents back reflection from the surface of or lower layers in the semiconductor devices and solves the problem of the CD being altered by the diffracted and reflected light from such lower layers.

44 Claims, No Drawings

ORGANIC ANTI-REFLECTIVE COATING MATERIAL AND ITS PREPARATION

CROSS-REFERENCES TO RELATED APPLICATIONS

This application is related to Korean Patent Application No. 99-8668, filed Mar. 15, 1999, and takes priority from that date.

BACKGROUND OF THE INVENTION

1. Field of the Invention

The present invention relates to an organic anti-reflective coating material which allows the stable formation of ultrafine patterns suitable for 64M, 256M, 1 G, 4 G and 16 G DRAM semiconductor devices. More particularly, the present invention relates to an organic anti-reflective coating material which contains a chromophore with high absorbance at the wavelengths useful for submicrolithography. A layer of said anti-reflection material can prevent back reflection of light from lower layers or the surface of the semiconductor chip, as well as eliminate the standing waves in the photoresist layer, during a submicrolithographic process using a 248 nm KrF, 193 nm ArF or 157 nm $F_2$ laser light sources. Also, the present invention is concerned with an anti-reflective coating composition comprising such a material, an anti-reflective coating therefrom and a preparation method thereof.

2. Description of the Prior Art

During a submicrolithographic process, one of the most important processes for fabricating highly integrated semiconductor devices, there inevitably occur standing waves and reflective notching of the waves due to the optical properties of lower layers coated on the wafer and to changes in the thickness of the photosensitive film applied thereon. In addition, the submicrolithographic process generally suffers from a problem of the CD (critical dimension) being altered by diffracted and reflected light from the lower layers.

To overcome these problems, it has been proposed to introduce a film, called an anti-reflective coating (hereinafter sometimes referred to as "ARC"), between the substrate and the photosensitive film. Generally, ARCs are classified as "organic" and "inorganic" depending on the materials used, and as "absorptive" and "interfering" depending on the mechanism of operation. In microlithographic processes using I-line (365 nm wavelength) radiation, inorganic ARCs, for example TiN or amorphous carbon coatings, are employed when advantage is taken of an absorption mechanism, and SiON coatings are employed when an interference mechanism is employed. The SiON ARCs are also adapted for submicrolithographic processes which use KrF light sources.

Recently, extensive and intensive research has been and continues to be directed to the application of organic ARCs for such submicrolithography. In view of the present development status, organic ARCs must satisfy the following fundamental requirements to be useful:

First, the peeling of the photoresist layer due to dissolution in solvents in the organic ARC should not take place when conducting a lithographic process. In this regard, the organic ARC materials have to be designed so that their cured films have a crosslinked structure without producing by-products.

Second, there should be no migration of chemical materials, such as amines or acids, into and from the ARCs. If acids are migrated from the ARC, the photosensitive patterns are undercut while the egress of bases, such as amines, causes a footing phenomena.

Third, faster etch rates should be realized in the ARC than in the upper photosensitive film, allowing an etching process to be conducted smoothly with the photosensitive film serving as a mask.

Finally, the organic ARCs should be as thin as possible while playing an excellent role in preventing light reflection.

Despite the variety of ARC materials, those which are satisfactorily applicable to submicrolithographic processes using ArF light have not been found, thus far. As for inorganic ARCs, there have been reported no materials which can control the interference at the ArF wavelength, that is, 193 nm. As a result, active research has been undertaken to develop organic materials which act as superb ARCs. In fact, in most cases of submicrolithography, photosensitive layers are necessarily accompanied by organic ARCs which prevent the standing waves and reflective notching occurring upon light exposure, and eliminate the influence of the back diffraction and reflection of light from lower layers. Accordingly, the development of such an ARC material showing high absorption properties against specific wavelengths is one of the hottest and most urgent issues in the art.

U.S. Pat. No. 4,910,122 discloses an ARC which is interposed under photosensitive layers to eliminate defects caused by reflected light. The coating described therein can be formed thinly, smoothly and uniformly and includes a light absorbing dye which eliminates many of the defects caused by reflected light, resulting in increased sharpness of the images in photosensitive materials. These types of ARCs, however, suffer from disadvantages of being complicated in formulation, extremely limited in material selection and difficult to apply for photolithography using Deep Ultraviolet (DUV) radiation. For example, the ARC of the above reference comprises 4 dye compounds, including polyamic acid, curcumin, Bixin and Sudan Orange G, and 2 solvents, including cyclohexanone and N-methyl-2-pyrrolidone. This multi-component system is not easy to formulate and may intermix with the resist composition coated thereover, bringing about undesired results.

SUMMARY OF THE INVENTION

Therefore, it is an object of the present invention to overcome the problems encountered in the prior art and to provide a novel organic compound which can be used as an ARC for submicrolithography using 193 nm ArF, 248 nm KrF and 157 nm $F_2$ lasers.

It is another object of the present invention to provide a method for preparing an organic compound which prevents the diffusion and reflection caused by the light exposure in submicrolithography.

It is a further object of the present invention to provide an ARC composition containing such a diffusion/reflection-preventive compound and a preparation method therefor.

It is a still further object of the present invention to provide an ARC formed from such a composition and a preparation method therefor.

The present invention pertains to acrylate polymer resins which can be used as an ARC. Preferred polymer resins contain a chromophore which exhibits high absorbance at 193 nm and 248 nm wavelengths. A crosslinking mechanism between alcohol groups and other functional groups is introduced into the polymer resins, so that a crosslinking reaction takes place when coatings of the polymer resins are "hard baked", thereby greatly improving the formation, tightness and dissolution properties of the ARCs. In particular, optimum crosslinking reaction efficiency and storage stability are realized in the present invention. The ARC resins of the present invention show superior solubility in all hydrocarbon solvents, but are of so high solvent resistance after hard baking that they are not dissolved in any solvent at all. These advantages allow the resins to be coated without any problem, and the coating prevents the undercutting and footing problems which can occur upon forming images on photosensitive materials. Furthermore, the coatings made of the acrylate polymers of the present invention are higher in etch rate than photosensitive films, improving the etch selection ratio therebetween.

DETAILED DESCRIPTION OF THE INVENTION

The ARC resins of the present invention are selected from the group consisting of acrylate polymers represented by the following general formulas I and II:

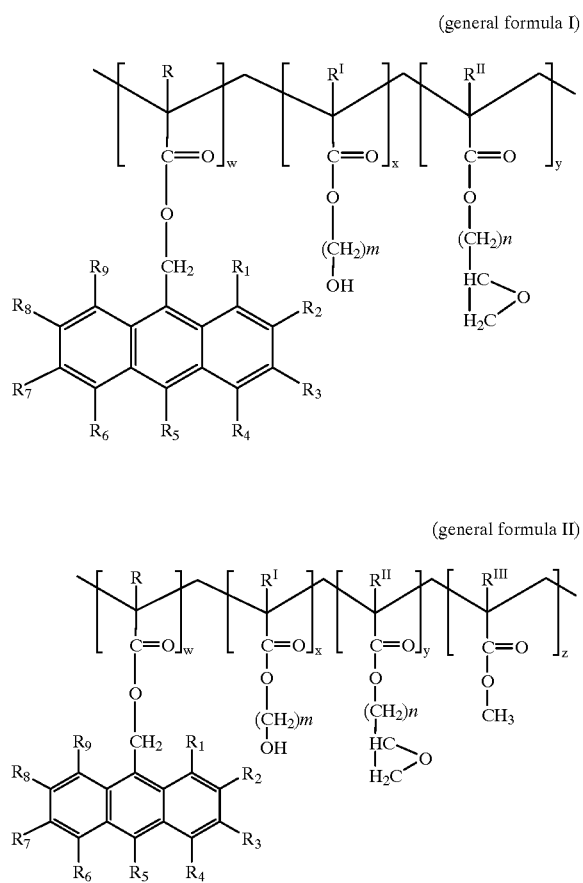

(general formula I)

(general formula II)

wherein,

R, $R^I$, $R^{II}$ and $R^{III}$ are independently hydrogen or a methyl group;

$R_1$ to $R_9$, which are the same or different, each represents hydrogen, hydroxy, methoxycarbonyl, carboxyl, hydroxymethyl, or a substituted or unsubstituted, linear or branched $C_1$–$C_5$ alkyl, alkane, alkoxyalkyl or alkoxyalkane;

x, y and z each is a mole fraction in the range from 0.01 to 0.99; and m and n are independently an integer of 1 to 4. In a preferred compound of Formula I, m is 1 or 2 and n is an integer of 1 to 4. In a preferred compound of Formula II, m is 1 or 2 and n is an integer from 2 to 4.

The polymers of the present invention are designed to provide high absorbance at the desired photolithographic wavelengths, e.g. 193 nm and 248 nm wavelengths. To accomplish this result chromophore substituents which are able to absorb the light at the desired wavelenths are grafted to the backbone of the polymer.

The polymers of general formula I can be prepared by polymerizing 9-anthracenemethyl acrylate type monomers, hydroxy alkylacrylate type monomers, and glycidyl acrylate type monomers with the aid of an initiator in a solvent. Each of the monomers has a mole fraction ranging from 0.01 to 0.99.

The polymers of general formula II can be prepared in a similar manner to the polymers of general formula I, using 9-anthracenemethyl acrylate type monomers, hydroxy alkylacrylate type monomers, glycidyl acrylate type monomers and methylmethacrylate type monomers at a mole fraction of 0.01 to 0.99 for each monomer.

For initiating the polymerization reaction for the polymers of the general formulas I and II, ordinary initiators may be used with preference given to 2,2-azobisisobutyronitrile (AIBN), acetylperoxide, laurylperoxide and t-butylperoxide. Also, ordinary solvents may be used for the polymerization. Preferably the solvent is selected from the group consisting of tetrahydrofuran, toluene, benzene, methylethyl ketone and dioxane.

Preferably, the polymerization of the polymers of the general formulas I and II is carried out at 50–90° C.

Also, the present invention pertains to an anti-reflective coating composition which comprises the polymer of the general formula I or II in combination with at least one additive selected from the group consisting of the anthracene derivatives shown in Table 1, below.

TABLE 1

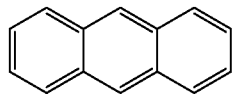

anthracene
Chemical Formula 1

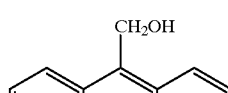

9-anthracenemethanol
Chemical Formula 2

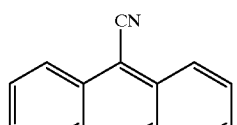

9-anthracenecarbonitrile
Chemical Formula 3

TABLE 1-continued

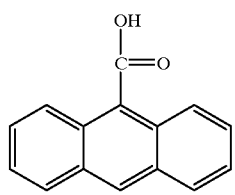

9-anthracenecarboxylic acid

Chemical Formula 4

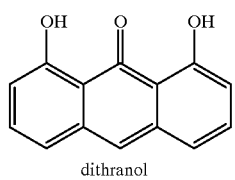

dithranol

Chemical Formula 5

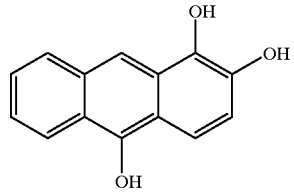

1,2,10-anthracenetriol

Chemical Formula 6

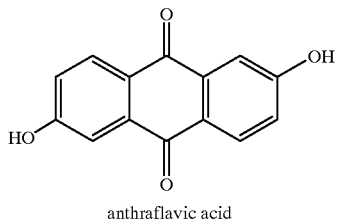

anthraflavic acid

Chemical Formula 7

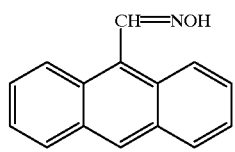

9-anthraldehyde oxime

Chemical Formula 8

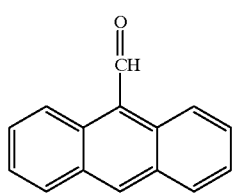

9-anthraldehyde

Chemical Formula 9

TABLE 1-continued

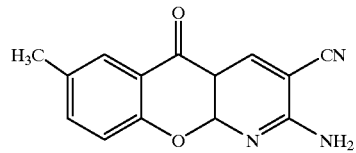

2-amino-7-methyl-5-oxo-5H-
[1]benzopyranol[2,3-b]
pyridine-3-carbonitrile

Chemical Formula 10

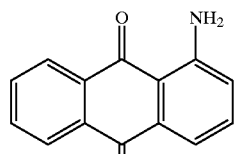

1-aminoanthraquinone

Chemical Formula 11

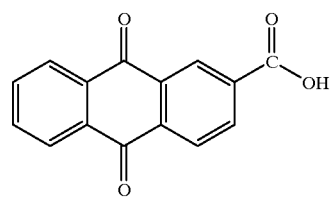

anthraquinone-2-carboxylic acid

Chemical Formula 12

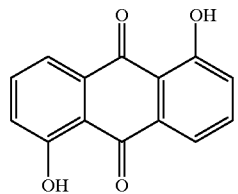

1,5-dihydroxyanthraquinone

Chemical Formula 13

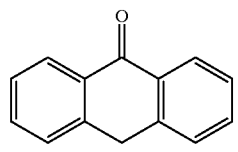

anthrone

Chemical Formula 14

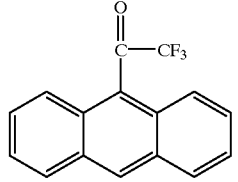

9-anthryl trifluoromethyl ketone

Chemical Formula 15

TABLE 1-continued

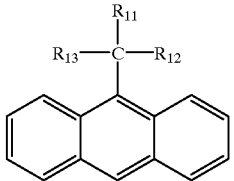

9-alkyl anthracene derivatives
Chemical Formula 16

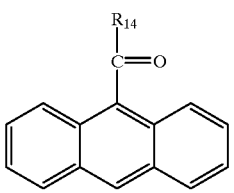

9-carboxyl anthracene derivatives
Chemical Formula 17

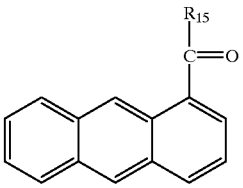

1-carboxyl anthracene derivatives
Chemical Formula 18

In Table 1, $R_{11}$, $R_{12}$, $R_{13}$, $R_{14}$ and $R_{15}$ independently represent hydrogen, hydroxy, hydroxymethyl, or substituted or unsubstituted linear or branched $C_1$–$C_5$ alkyl, alkane, alkoxyalkyl or alkoxyalkane.

Anti-reflective coating compositions according to the present invention may be prepared by (i) adding the compound selected from the Table 1, at an amount of 0.1 to 30% by weight to a solution of the polymer of the general formula I or II in a solvent and (ii) filtering the solution. This coating composition may be applied on a wafer in a conventional manner and then hard-baked (heated to a temperature of 100–300° C. for 10–1000 seconds) to form a crosslinked anti-reflective coating. Quality semiconductor devices can be fabricated using anti-reflective coatings of the present invention.

Ordinary organic solvents may be used in preparing the composition, with preference given to ethyl 3-ethoxypropionate, methyl 3-methoxy propionate, cyclohexanone and propylene methyletheracetate. The solvent is preferably used at an amount of 200 to 5000% by weight based on the total weight of the anti-reflective coating resin polymers used.

It has been found that the anti-reflective coatings of the present invention exhibit high performance in submicrolithographic processes using 248 nm KrF, 193 nm ArF and 157 nm $F_2$. lasers as light sources. The same was also true when E-beams, EUV (extreme ultraviolet) and ion beams are used as light sources.

The following examples are set forth to illustrate more clearly the principles and practice of this invention to one skilled in the art. As such, they are not intended to limit the invention, but are illustrative of certain preferred embodiments.

EXAMPLE I

Synthesis if Poly[9-anthracenemethylacrylate-(2-hydroxyethylacrylate)-glycidylmethacrylate] Copolymer Synthesis of 9-anthracenemethylacrylate 0.5 moles of 9-anthracene methanol and 0.5 moles of pyridine are dissolved in tetrahydrofuran and then 0.5 moles of acryloyl chloride are added. After completion of the reaction, the product is filtered out and extracted with ethyl acetate, The extract is washed many times with distilled water and dried by distillation under vacuum, to give 9-anthracenemethylacrylate, represented by the following chemical formula 19. (Yield 84%).

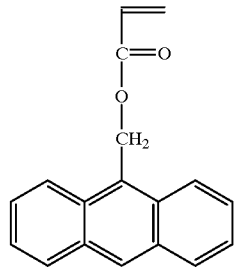

(chemical formula 19)

Synthesis of Poly[9-anthracenemethylacrylate-(2-hydroxyethylacrylate)-glycidylmethacrylate] Copolymer In a 500 ml round-bottom flask are placed 0.5 moles of the 9-anthracenemethylacrylate synthesized above, 0.3 moles of 2-hydroxyethylacrylate, and 0.2 moles of glycidylmethacrylate. This mixture is added to 300 g of separately prepared tetrahydrofuran (THF) with stirring. Thereafter, in the presence of 0.1–3 g of 2,2-azobisisobutyronitrile (MIBN), the reaction mixture is subjected to polymerization at 60–75° C. for 5–20 hours in a nitrogen atmosphere. After completion of the polymerization, the solution is precipitated in ethyl ether or normal-hexane and the precipitate is filtered out and dried to produce poly[9-anthracenemethylacrylate-(2-hydroxyethylacrylate)-glycidylmethacrylate] copolymer, a polymer according to the present invention, at a yield of 80%.

EXAMPLE II

Synthesis of Poly[9-anthracenemethylacrylate-(3-hydroxypropylacrylate)-glycidylmethacrylate] Copolymer In a 500 ml round-bottom flask are placed 0.5 moles of the 9-anthracenemethylacrylate synthesized in Example I, 0.3 moles of 3-hydroxypropylacrylate, and 0.2 moles of glycidylmethacrylate. This mixture is added to 300 g of separately prepared THF with stirring. Thereafter, in the presence of 0.1–3 g of AIBN, the reaction mixture is subjected to polymerization at 60–75° C. for 5–20 hours in a nitrogen atmosphere. After completion of the polymerization, the solution is precipitated in ethyl ether or normal-hexane and the precipitate is filtered out and dried to produce a poly[9-anthracenemethylacrylate-(3-hydroxypropylacrylate)-glycidylmethacrylate] copolymer, a polymer according to the present invention, at a yield of 79%.

EXAMPLE III

Synthesis of Poly[9-anthracenemethylacrylate-(2-hydroxyethylacrylate)-glycidylacrylate] Copolymer In a 500 ml round-bottom flask are placed 0.5 moles of 9-anthracenemethylacrylate, 0.3 moles of 2-hydroxyethylacrylate, and 0.2 moles of glycidylacrylate. This mixture is added to 300 g of separately prepared THF with stirring. Thereafter, in the presence of 0.1–3 g of AIBN, the reaction mixture is subjected to polymerization at 60–75° C. for 5–20 hours in a nitrogen atmosphere. After completion of the polymerization, the solution is precipitated in ethyl ether or normal-hexane and the precipitate is filtered out and dried to produce a poly[9-anthracenemethylacrylate-(2-hydroxyethylacrylate)-glycidylacrylate] copolymer, a polymer according to the present invention. (Yield 81%).

EXAMPLE IV

Synthesis of Poly[9-anthracenemethylacrylate-(3-hydroxypropylacrylate)-glycidylacrylate] Copolymer In a 500 ml round-bottom flask are placed 0.5 moles of 9-anthracenemethylacrylate, 0.3 moles of 3-hydroxypropylacrylate, and 0.2 moles of glycidylacrylate. This mixture is added to 300 g of separately prepared THF with stirring. Thereafter, in the presence of 0.1–3 g of AIBN, the reaction mixture is subjected to polymerization at 60–75° C. for 5–20 hours in a nitrogen atmosphere. After completion of the polymerization, the solution is precipitated in ethyl ether or normal-hexane and the precipitate is filtered out and dried to produce a poly[9-anthracenemethylacrylate-(3-hydroxypropylacrylate)-glycidylacrylate] copolymer, a polymer according to the present invention, at a yield of 78%.

EXAMPLE V

Synthesis of Poly[9-anthracenemethylacrylate-(4-hydroxybutlacrylate)-glycidylacrylate] Copolymer In a 500 ml round-bottom flask are placed 0.5 moles of 9-anthracenemethylacrylate, 0.3 moles of 4-hydroxybutylacrylate, and 0.2 moles of glycidylacrylate. This mixture is added to 300 g of separately prepared THF with stirring, after which, in the presence of 0.1–3 g of AIBN, the reaction mixture is subjected to polymerization at 60–75° C. for 5–20 hours in a nitrogen atmosphere. After completion of the polymerization, the solution is precipitated in ethyl ether or normal-hexane and the precipitate is filtered out and dried to produce a poly[9-anthracenemethylacrylate-(4-hydroxybutylacrylate)-glycidylacrylate] copolymer, a polymer according to the present invention. (Yield 80%).

EXAMPLE VI

Synthesis of Poly[9-anthracenemethylmethacrylate-(2-hydroxyethylacrylate)-glycidylmethacrylate] Copolymer Synthesis of 9-Anthracenemethylmethacrylate 0.5 moles of 9-anthracene methanol and 0.5 moles of pyridine are dissolved in THF and then, 0.5 moles of methacryloyl chloride are added. After completion of this reaction, the product is filtered out, extraction is conducted with ethyl acetate. The extract is washed many times with distilled water and dried by distillation under vacuum, to give 9-anthracenemethylmethacrylate, represented by the following chemical formula 20. (Yield 83%).

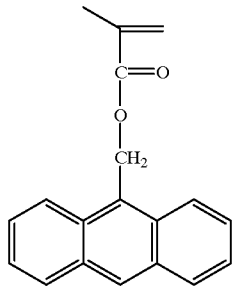

(chemical formula 20)

Synthesis of Poly[9-anthracenemethylmethacrylate-(2-hydroxyethylacrylate-glycidylmethacrylate] Copolymer In a 500 ml round-bottom flask are placed 0.5 moles of the 9-anthracenemethylmethacrylate synthesized above, 0.3 moles of 2-hydroxyethylacrylate, and 0.2 moles of glycidylmethacrylate. This mixture is added to 300 g of separately prepared tetrahydrofuran (THF) with stirring. Thereafter, in the presence of 0.1–3 g of 2,2-azobisisobutyronitrile (AIBN), the reaction mixtures subjected to polymerization at 60–75° C. for 5–20 hours in a nitrogen atmosphere. After completion of the polymerization, the solution is precipitated in ethyl ether or normal-hexane and the precipitate is filtered out and dried to produce a poly[9-anthracenemethylmethacrylate-(2-hydroxyethylacrylate) glycidylmethacrylate] copolymer, a polymer according to the present invention, at a yield of 77%.

EXAMPLE VII

Synthesis of Poly[9-anthracenemethylmethacrylate-(3-hydroxypropylacrylate)-glycidylmethacrylate] Copolymer In a 500 ml round-bottom flask are placed 0.5 moles of the 9-anthracenemethylmethacrylate synthesized in Example VI, 0.3 moles of 3-hydroxypropylacrylate, and 0.2 moles of glycidylmethacrylate. This mixture is added to 300 g of separately prepared THF with stirring, after which, in the presence of 0.1–3 g of AIBN, the reaction mixture is subjected to polymerization at 60–75° C. for 5–20 hours in a nitrogen atmosphere. After completion of the polymerization, the solution is precipitated in ethyl ether or normal-hexane and the precipitate is filtered out and dried to produce a poly[9-anthracenemethylmethacrylate-(3-hydroxypropylacrylate)-glycidylmethacrylate] copolymer, a polymer according to the present invention, at a yield of 80%.

EXAMPLE VIII

Synthesis of Poly[9-anthracenemethylacrylate-(4-hydroxybutylacrylate)-glycidylmethacrylate] Copolymer In a 500 ml round-bottom flask are placed 0.5 moles of 9-anthracenemethylmethacrylate, 0.3 moles of 2-hydroxybutylacrylate, and 0.2 moles of glycidylmethacrylate. This mixture is added to 300 g of separately prepared THF with stirring. Thereafter, in the presence of 0.1–3 g of AIBN, the reaction mixture is subjected to polymerization at 60–75° C. for 5–20 hours in a nitrogen atmosphere. After completion of the polymerization, the solution is precipitated in ethyl ether or normal-hexane and the precipitate is filtered out and dried to produce a poly[9-anthracenemethylmethacrylate-(4-hydroxybutylacrylate)-glycidylmethacrylate] copolymer, a polymer according to the present invention. (Yield 80%).

EXAMPLE IX

Synthesis of Poly[9-anthracenemethylmethacrylate-(4-hydroxybutylacrylate)-glycidylacrylate] Copolymer In a 500 ml round-bottom flask are placed 0.5 moles of 9-anthracenemethylmethacrylate, 0.3 moles of 4-hydroxybutylacrylate, and 0.2 moles of glycidylacrylate. This mixture is added to 300 g of separately prepared THF with stirring. Thereafter, in the presence of 0.1–3 g of AIBN, the reaction mixture is subjected to polymerization at 60–75° C. for 5–20 hours in a nitrogen atmosphere. After completion of the polymerization, the solution is precipitated in ethyl ether or normal-hexane and the precipitate is filtered out and dried to produce a poly[9-anthracenemethylmethacrylate-(4-hydroxybutylacrylate)-glycidylacrylate] copolymer, a polymer according to the present invention. (Yield 79%).

EXAMPLE X

Synthesis of Poly[9-anthracenemethylmethacrylate-(2-hydroxypropylacrylate)-glycidylacrylate] Copolymer In a 500 ml round-bottom flask are placed 0.5 moles of 9-anthracenemethylmethacrylate, 0.3 moles of 3-hydroxypropylacrylate, and 0.2 moles of glycidylacrylate. This mixture is added to 300 g of separately prepared THF with stirring. Thereafter, in the presence of 0.1–3 g of AIBN, the reaction mixture is subjected to polymerization at 60–75° C. for 5–20 hours in a nitrogen atmosphere. After completion of the polymerization, the solution is precipitated in ethyl ether or normal-hexane and the precipitate is filtered out and dried to produce a poly[9-anthracenemethylmethacrylate-(3-hydroxypropylacrylate)-glycidylacrylate] copolymer, a polymer according to the present invention. (Yield 81%).

EXAMPLE XI

Synthesis of Poly[9-anthracenemethylmethacrylate-(4-hydroxyethylacrylate)-glycidylacrylate] Copolymer In a 500 ml round-bottom flask are placed 0.5 moles of 9-anthracenemethylmethacrylate, 0.3 moles of 4hydroxyethylacrylate, and 0.2 moles of glycidylacrylate. This mixture is added to 300 g of separately prepared THF with stirring. Thereafter, in the presence of 0.1–3 g of AIBN, the reaction mixture is subjected to polymerization at 60–75° C. for 5–20 hours in a nitrogen atmosphere. After completion of the polymerization, the solution is precipitated in ethyl ether or normal-hexane and the precipitate is filtered out and dried to produce a poly[9-anthracenemethylmethacrylate-(4-hydroxyethylacrylate)-glycidylacrylate] copolymer, a polymer according to the present invention. (Yield 80%).

EXAMPLE XII

Synthesis of Poly[9-anthracenemethylacrylate-(2-hydroxyethylacrylate)-glycidylmethacrylate-methylmethacrylate] Copolymer In a 500 ml round-bottom flask are placed 0.3 moles of 9-anthracenemethylacrylate, 0.3 moles of 2-hydroxyethylacrylate, 0.2 moles of glycidylmethacrylate and 0.2 moles of methylmethacrylate. This mixture is added to 300 g of separately prepared THF with stirring. Thereafter, in the presence of 0.1–3 g of AIBN, the reaction mixture is subjected to polymerization at 60–75° C. for 5–20 hours in a nitrogen atmosphere. After completion of the polymerization, the solution is precipitated in ethyl ether or normal-hexane and the precipitate is filtered out and dried to produce a poly[9-anthracenemethylacrylate-(2-hydroxyethylacrylate)-glycidylmethacrylate-methylmethacrylate] copolymer, a polymer according to the present invention, at a yield of 81%.

EXAMPLE XIII

Synthesis of Poly[9-anthracenemethylacrylate-(3-hydroxypropylacrylate)-glycidylmethacrylate-methylmethacrylate] Copolymer In a 500 ml round-bottom flask are placed 0.3 moles of 9-anthracenemethylacrylate, 0.3 moles of 3-hydroxypropylacrylate, 0.2 moles of glycidylmethacrylate and 0.2 moles of methylmethacrylate. This mixture is added to 300 g of separately prepared THF with stirring. Thereafter, in the presence of 0.1–3 g of AIBN, the reaction mixture is subjected to polymerization at 60–75° C. for 5–20 hours in a nitrogen atmosphere. After completion of the polymerization, the solution is precipitated in ethyl ether or normal-hexane and the precipitate is filtered out and dried to produce a poly[9-anthracenemethylacrylate-(3-hydroxypropylacrylate)-glycidylmethacrylate-methylmethacrylate] copolymer, a polymer according to the present invention, at a yield of 79%.

EXAMPLE XIV

Synthesis of Poly[9-anthracenemethylacrylate-(2-hydroxyethylacrylate)-glycidylacrylate-methylmethacrylate] Copolymer In a 500 ml round-bottom flask are placed 0.3 moles of 9-anthracenemethylacrylate, 0.3 moles of 2-hydroxyethylacrylate, 0.2 moles of glycidylacrylate and 0.2 moles of methylmethacrylate. This mixture is added to 300 g of separately prepared THF with stirring. Thereafter, in the presence of 0.1–3 g of AIBN, the reaction mixture is subjected to polymerization at 60–75° C. for 5–20 hours in a nitrogen atmosphere. After completion of the polymerization, the solution is precipitated in ethyl ether or normal-hexane and the precipitate is filtered out and dried to produce a poly[9-anthracenemethylacrylate-(2-hydroxyethylacrylate)-glycidylacrylate-methylmethacrylate] copolymer, a polymer according to the present invention, at a yield of 80%.

EXAMPLE XV

Synthesis of Poly[9-anthracenemethylacrylate-(3-hydroxypropylacrylate)-glycidylacrylate-methylmethacrylate] Copolymer In a 500 ml round-bottom flask are placed 0.3 moles of 9-anthracenemethylacrylate, 0.3 moles of 3-hydroxypropylacrylate, 0.2 moles of glycidylacrylate and 0.2 moles of methylmethacrylate. This mixture is added to 300 g of separately prepared THF with stirring. Thereafter, in the presence of 0.1–3 g of AIBN, the reaction mixture is subjected to polymerization at 60–75° C. for 5–20 hours in a nitrogen atmosphere. After completion of the polymerization, the solution is precipitated in ethyl ether or normal-hexane and the precipitate is filtered out and dried to produce a poly[9-anthracenemethylacrylate-(3-hydroxypropylacrylate)-glycidylacrylate-methylmethacrylate] copolymer, a polymer according to the present invention, at a yield of 79%.

EXAMPLE XVI

Synthesis of Poly[9-anthracenemethylacrylate-(4-hydroxybutylacrylate)-glycidylacrylate-methylmethacrylate] Copolymer In a 500 ml round-bottom flask are placed 0.3 moles of 9-anthracenemethylacrylate, 0.3 moles of 4-hydroxybutylacrylate, 0.2 moles of glycidylacrylate and 0.2 moles of methylmethacrylate. This mixture is added to 300 g of separately prepared THF with stirring. Thereafter, in the presence of 0.1–3 g of AIBN, the reaction mixture is subjected to polymerization at 60–75° C. for 5–20 hours in a nitrogen atmosphere. After completion of the polymerization, the solution is precipitated in ethyl ether or normal-hexane and the precipitate is filtered out and dried to produce a poly[9-anthracenemethylacrylate-(4-hydroxybutylacrylate)-glycidylacrylate-methylmethacrylate] copolymer, a polymer according to the present invention, at a yield of 81%.

EXAMPLE XVII

Synthesis of Poly[9-anthracenemethylmethacrylate-(2-hydroxyethylacrylate)-glycidylmethacrylate-methylmethacrylate] Copolymer In a 500 ml round-bottom flask are placed 0.3 moles of 9-anthracenemethylmethacrylate, 0.3 moles of 2-hydroxyethylacrylate, 0.2 moles of glycidylmethacrylate and 0.2 moles of methylmethacrylate. This mixture is added to 300 g of separately prepared THF with stirring, after which, in the presence of 0.1–3 g of AIBN, the reaction mixture is subjected to polymerization at 60–75° C. for 5–20 hours in a nitrogen atmosphere. After completion of the polymerization, the solution is precipitated in ethyl ether or normal-hexane and the precipitate is filtered out and dried to produce a poly[9-anthracenemethylmethacrylate-(2-hydroxyethylacrylate)-glycidylmethacrylate-methylmethacrylate] copolymer, a polymer according to the present invention. (Yield 79%).

EXAMPLE XVIII

Synthesis of Poly[9-anthracenemethylmethacrylate-(3-hydroxypropylacrylate)-glycidylmethacrylate-methylmethacrylate] Copolymer In a 500 ml round-bottom flask are placed 0.3 moles of 9-anthracenemethylmethacrylate, 0.3 moles of 3-hydroxypropylacrylate, 0.2 moles of glycidylmethacrylate and 0.2 moles of methylmethacrylate. This mixture is added to 300 g of separately prepared THF with stirring. Thereafter, in the presence of 0.1–3 g of AIBN, the reaction mixture is subjected to polymerization at 60–75° C. for 5–20 hours in a nitrogen atmosphere. After completion of the polymerization, the solution is precipitated in ethyl ether or normal-hexane and the precipitate is filtered out and dried to produce a poly[9-anthracenemethylmethacrylate-(3-hydroxypropylacrylate)-glycidylmethacrylate-methylmethacrylate] copolymer, a polymer according to the present invention, at a yield of 79%.

EXAMPLE XIX

Synthesis of Poly[9-anthracenemethylmethacrylate-(4-hydroxybutylacrylate)-glycidylmethacrylate-methylmethacrylate] Copolymer In a 500 ml round-bottom flask are placed 0.3 moles of 9-anthracenemethylmethacrylate, 0.3 moles of 4hydroxybutylacrylate, 0.2 moles of glycidylmethacrylate and 0.2 moles of methylmethacrylate. This mixture is added to 300 g of separately prepared THF with stirring. Thereafter, in the presence of 0.1–3 g of AIBN, the reaction mixture is subjected to polymerization at 60–75° C. for 5–20 hours in a nitrogen atmosphere. After completion of the polymerization, the solution is precipitated in ethyl ether or normal-hexane and the precipitate is filtered out and dried to produce a poly[9-anthracenemethylmethacrylate-(4-hydroxybutylacrylate)-glycidylmethacrylate-methylmethacrylate] copolymer, a polymer according to the present invention, at a yield of 80%.

EXAMPLE XX

Synthesis of Poly[9-anthracenemethylmethacrylate-(2-hydroxyethylacrylate)-glycidylacrylate-methylmethacrylate] Copolymer In a 500 ml round-bottom flask are placed 0.3 moles of 9-anthracenemethylmethacrylate, 0.3 moles of 2-hydroxyethylacrylate, 0.2 moles of glycidylacrylate and 0.2 moles of methylmethacrylate. This mixture is added to 300 g of separately prepared THF with stirring. Thereafter, in the presence of 0.1–3 g of AIBN, the reaction mixture is subjected to polymerization at 60–75° C. for 5–20 hours in a nitrogen atmosphere. After completion of the polymerization, the solution is precipitated in ethyl ether or normal-hexane and the precipitate is filtered out and dried to produce a poly[9-anthracenemethylmethacrylate-(2-hydroxyethylacrylate)-glycidylacrylate-methylmethacrylate] copolymer, a polymer according to the present invention. (Yield 80%).

EXAMPLE XXI

Synthesis of Poly[9-anthracenemethylmethacrylate-(3-hydroxypropylacrylate)-glycidylacrylate-methylmethacrylate] Copolymer In a 500 ml round-bottom flask are placed 0.3 moles of 9-anthracenemethylmethacrylate, 0.3 moles of 4-hydroxypropylacrylate, 0.2 moles of glycidylacrylate and 0.2 moles of methylmethacrylate. This mixture is added to 300 g of separately prepared THF with stirring. Thereafter, in the presence of 0.1–3 g of AIBN, the reaction mixture is subjected to polymerization at 60–75° C. for 5–20 hours in a nitrogen atmosphere. After completion of the polymerization, the solution is precipitated in ethyl ether or normal-hexane and the precipitate is filtered out and dried to produce a poly[9-anthracenemethylacrylate-(3-hydroxypropylacrylate)-glycidylacrylate-methylmethacrylate] copolymer, a polymer according to the present invention. (Yield 80%).

EXAMPLE XXII

Synthesis of Poly[9-anthracenemethylmethacrylate-(4-hydroxyethylacrylate)-glycidylacrylate-methylmethacrylate] Copolymer In a 500 ml round-bottom flask are placed 0.3 moles of 9-anthracenemethylmethacrylate, 0.3 moles of 4-hydroxybutylacrylate, 0.2 moles of glycidylacrylate and 0.2 moles of methylmethacrylate. This mixture is added to 300 g of separately prepared THF with stirring. Thereafter, in the presence of 0.1–3 g of AIBN, the reaction mixture is subjected to polymerization at 60–75° C. for 5–20 hours in a nitrogen atmosphere. After completion of the polymerization, the solution is precipitated in ethyl ether or normal-hexane and the precipitate is filtered out and dried to produce a poly[9-anthracenemethylmethacrylate-(4-hydroxybutylacrylate)-glycidylacrylate-methylmethacrylate] copolymer, a polymer according to the present invention. (Yield 81%).

EXAMPLE XXIII

Preparation of Anti-reflective Coating

In 200–5,000% by weight of propyleneglycol methylether acetate (PGMEA) is dissolved a polymer (resin) having a chemical structure of general formula I or II above, e.g. as obtained in Examples I to XXI. This solution, alone or in combination with 0.1–30% by weight of at least one additive selected from the compounds of the chemical formulas 1 to 18 in Table 1, is filtered, coated on a wafer, and "hard-baked" (i.e. heated at 100–300° C. for 10–1,000 sec). On the anti-reflective coating thus formed, a photosensitive material may be applied and imaged to ultrafine patterns in the conventional manner.

As described hereinbefore, the anti-reflective coating of the present invention, which is obtained from the polymer of the general formula I or II, alone or in combination with the additive of one of the chemical formulas 1 to 18, contains chromophore substituents sufficient to exhibit absorbance at the wavelengths useful for submicrolithography. Thus, the anti-reflective coating of the present invention can play an excellent role in forming ultrafine patterns. For example, it can prevent the back reflection of light from the wafer surface and lower layers as well as eliminate the standing waves in the photoresist layer itself during a submicrolithographic process using 248 nm KrF, 193 nm ArF or 157 nm $F_2$ laser. This results in the formation of stable ultrafine patterns suitable for 64M, 256M, 1 G, 4 G and 16 G DRAM semiconductor devices and a great improvement in the production yield.

Although the invention has been described in detail by referring to certain preferred embodiments, it will be understood that various modifications can be made within the spirit and scope of the invention. The invention is not to be limited except as set forth in the following claims.

What is claimed is:

1. A polymer represented by the following general formula I:

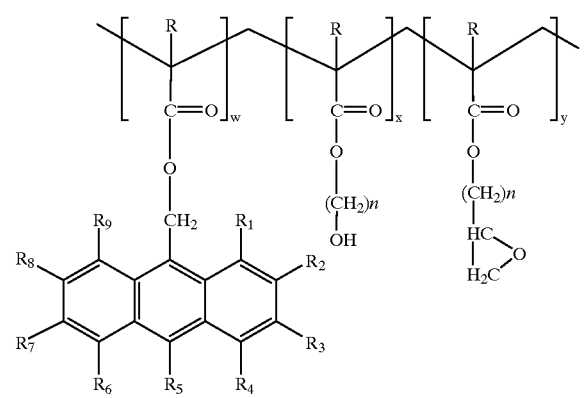

(general formula I)

wherein,
R is hydrogen or a methyl group;
$R_1$ to $R_9$, which are the same or different, each represents hydrogen, hydroxy, methoxycarbonyl, carboxyl, hydroxymethyl, or a substituted or unsubstituted, linear or branched $C_1$–$C_5$ alkyl, alkane, alkoxyalkyl or alkoxyalkane;
w, x and y each is a mole fraction in the range from 0.01 to 0.99; and
n is an integer of 1 to 4.

2. A polymer as set forth in claim 1, wherein R is hydrogen or a methyl group, $R_1$ to $R_9$ each is hydrogen, w, x and y each is a mole fraction ranging from 0.01 to 0.99, and n is an integer of 1 to 4.

3. A polymer as set forth in claim 1 comprising poly[9-anthracenemethylacrylate-(2-hydroxyethyl acrylate)-glycidylmethacrylate] wherein the mole ratio of 9-anthracenemethylacrylate:2-hydroxyethyl acrylate:glycidylmethacrylate is 5:3:2.

4. A polymer as set forth in claim 1 comprising poly[9-anthracenemethylacrylate-(3-hydroxypropyl acrylate)-glycidylmethacrylate] wherein the mole ratio of 9-anthracenemethylacrylate:3-hydroxypropyl acrylate:glycidylmethacrylate is 5:3:2.

5. A polymer as set forth in claim 1 comprising poly[9-anthracenemethylacrylate-(2-hydroxyethyl acrylate)-glycidylacrylate] wherein the mole ratio of 9-anthracenemethylacrylate:2-hydroxyethyl acrylate:glycidylacrylate is 5:3:2.

6. A polymer as set forth in claim 1 comprising poly[9-anthracenemethylacrylate-(3-hydroxypropyl acrylate)-glycidylacrylate] wherein the mole ratio of 9-anthracenemethylacrylate:3-hydroxypropyl acrylate:glycidylacrylate is 5:3:2.

7. A polymer as set forth in claim 1 comprising poly[9-anthracenemethylacrylate-(4-hydroxybutyl acrylate)-glycidylacrylate] wherein the mole ratio of 9-anthracenemethylacrylate:4-hydroxybutyl acrylate:glycidylacrylate is 5:3:2.

8. A polymer as set forth in claim 1 comprising poly[9-anthracenemethylmethacrylate-(2-hydroxyethyl acrylate)-glycidylmethacrylate] wherein the mole ratio of 9-anthracenemethylmethacrylate:2-hydroxyethyl acrylate:glycidylmethacrylate is 5:3:2.

9. A polymer as set forth in claim 1 comprising poly[9-anthracenemethylmethacrylate-(3-hydroxypropyl acrylate)-glycidylmethacrylate] wherein the mole ratio of 9-anthracenemethylmethacrylate:3-hydroxypropyl acrylate:glycidylmethacrylate is 5:3:2.

10. A polymer as set forth in claim 1 comprising poly[9-anthracenemethylmethacrylate-(4-hydroxybutyl acrylate)-glycidylmethacrylate] wherein the mole ratio of 9-anthracenemethylmethacrylate:4-hydroxybutyl acrylate:glycidylmethacrylate is 5:3:2.

11. A polymer as set forth in claim 1 comprising poly[9-anthracenemethylmethacrylate-(2-hydroxyethyl acrylate)-glycidylacrylate] wherein the mole ratio of 9-anthracenemethylmethacrylate:2-hydroxyethyl acrylate:glycidylacrylate is 5:3:2.

12. A polymer as set forth in claim 1 comprising poly[9-anthracenemethylmethacrylate-(3-hydroxypropyl acrylate)-glycidylacrylate] wherein the mole ratio of 9-anthracenemethylmethacrylate:3-hydroxypropyl acrylate:glycidylacrylate is 5:3:2.

13. A polymer as set forth in claim 1 comprising poly[9-anthracenemethylmethacrylate-(4-hydroxybutyl acrylate)-glycidylacrylate] wherein the mole ratio of 9-anthracenemethylmethacrylate:4-hydroxybutyl acrylate:glycidylacrylate is 5:3:2.

14. A method for preparing a polymer of claim 1 comprising polymerizing in a solvent with the aid of an initiator; (i) a 9-anthracene methylacrylate monomer, (ii) an hydroxymethyl-, hydroxypropyl- or hydroxybutyl-acrylate monomer, and (iii) a glycidyl acrylate monomer.

15. A method as set forth in claim 14, wherein the molar ratio of monomer (i): monomer (ii): (iii) is in a range of 0.01–0.99:0.01–0.99:0.01–0.99.

16. A method as set forth in claim 14, wherein the initiator is selected from the group consisting of 2,2-azobisisobutyronitrile, acetylperoxide, laurylperoxide, and t-butylperoxide.

17. A method as set forth in claim 14, wherein the solvent is selected from the group consisting of tetrahydrofuran, toluene, benzene, methylethyl ketone and dioxane.

18. A method as set forth in claim 14, wherein the polymerization is carried out at a temperature of 50–90° C.

19. A polymer represented by the following general formula (general formula II)

$$\left[\begin{array}{c}R\\|\\C=O\\|\\O\\|\\CH_2\\R_9\underset{R_8\underset{R_7\underset{R_6\;R_5\;R_4}{}}{}}{}R_1\,R_2\,R_3\end{array}\right]_w\left[\begin{array}{c}R\\|\\C=O\\|\\O\\|\\(CH_2)_n\\|\\OH\end{array}\right]_x\left[\begin{array}{c}R\\|\\C=O\\|\\O\\|\\(CH_2)_n\\|\\HC\!\!-\!\!O\\H_2C\end{array}\right]_y\left[\begin{array}{c}R\\|\\C=O\\|\\O\\|\\CH_3\end{array}\right]_z$$

wherein,
R is hydrogen or a methyl group;
$R_1$ to $R_9$, which are the same or different, each represents hydrogen, hydroxy, methoxycarbonyl, carboxyl, hydroxymethyl, or a substituted or unsubstituted, linear or branched $C_1$–$C_5$ alkyl, alkane, alkoxyalkyl or alkoxyalkane;
w, x, y and z each is a mole fraction in the range from 0.01 to 0.99; and
n is an integer of 1, 3 or 4.

20. A polymer as set forth in claim 19, wherein R is hydrogen or a methyl group, $R_1$ to $R_9$ each is hydrogen, w, x, y and z each is a mole fraction ranging from 0.01 to 0.99, and n is an integer of 3 to 4.

21. A polymer as set forth in claim 19, comprising poly[9-anthracenemethylacrylate-(3-hydroxypropyl acrylate)-glycidylmethacrylate-methylmethacrylate] wherein the mole ratio of 9-anthracenemethylacrylate:3-hydroxypropyl acrylate:glycidylmethacrylate:methylmethacrylate is 3:3:2:2.

22. A polymer as set forth in claim 19, comprising poly[9-anthracenemethylacrylate-(3-hydroxypropyl acrylate)-glycidylacrylate-methylmethacrylate] wherein the mole ratio of 9-anthracenemethylacrylate:3-hydroxypropyl acrylate:glycidylacrylate:methylmethacrylate is 3:3:2:2.

23. A polymer as set forth in claim 19, comprising poly[9-anthracenemethylacrylate-(4-hydroxybutyl acrylate)-glycidylacrylate-methylmethacrylate] wherein the mole ratio of 9-anthracenemethylacrylate; 4-hydroxybutyl acrylate:glycidylacrylate:methylmethacrylate is 3:3:2:2.

24. A polymer as set forth in claim 19, comprising poly[9-anthracenemethylmethacrylate-(3-hydroxypropyl acrylate)-glycidylmethacrylate-methylmethacrylate] wherein the mole ratio of 9-anthracenemethylmethacrylate:3-hydroxypropyl acrylate:glycidylmethacrylate:methylmethacrylate is 3:3:2:2.

25. A polymer as set forth in claim 19, comprising poly[9-anthracenemethylmethacrylate-(4-hydroxybutyl acrylate)-glycidylmethacrylate-methylmethacrylate] wherein the mole ratio of 9-anthracenemethylmethacrylate: 4-hydroxybutyl acrylate:glycidylmethacrylate:methylmethacrylate is 3:3:2:2.

26. A polymer as set forth in claim 19, comprising poly[9-anthracenemethylmethacrylate-(3-hydroxypropyl acrylate)-glycidylacrylate-methylmethacrylate] wherein the mole ratio of 9-anthracenemethylmethacrylate:3-hydroxypropyl acrylate:glycidylacrylate:methylmethacrylate is 3:3:2:2.

27. A polymer as set forth in claim 19, comprising poly[9-anthracenemethylmethacrylate-(4hydroxybutyl acrylate)-glycidylacrylate-methylmethacrylate] wherein the mole ratio of 9-anthracenemethylmethacrylate:4-hydroxybutyl acrylate:glycidylacrylate:methylmethacrylate is 3:3:2:2.

28. A method for preparing a polymer of claim 19 comprising polymerizing in a solvent with the aid of an initiator, (i) a 9-anthracene methylacrylate monomer, (ii) a hydroxymethyl-, hydroxypropyl- or hydroxybutyl-acrylate monomer, (iii) a glycidyl acrylate monomer and (iii) a methylmethacrylate monomer.

29. A method as set forth in claim 28, wherein the molar ratio of monomer (i): monomer (ii): monomer (iii) is in a range of 0.01–0.99:0.01–0.99:0.01–0.99:0.01–0.99.

30. A method as set forth in claim 28, wherein the initiator is selected from the group consisting of 2,2-azobisisobutyronitrile, acetylperoxide, laurylperoxide, and t-butylperoxide.

31. A method as set forth in claim 28, wherein the solvent is selected from the group consisting of tetrahydrofuran, toluene, benzene, methylethyl ketone and dioxane.

32. A method as set forth in claim 28, wherein the polymerization is carried out at a temperature of 50–90° C.

33. An anti-reflective coating useful for the fabrication of semiconductor devices, comprising a polymer of claim 1.

34. An anti-reflective coating, useful for the fabrication of semiconductor devices, comprising a polymer of claim 19.

35. An anti-reflective coating, comprising a polymer of claim 1 or a polymer of claim 19 and at least one compound selected from the group consisting of the compounds in the following Table 1:

TABLE 1

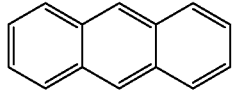

anthracene
Chemical Formula 1

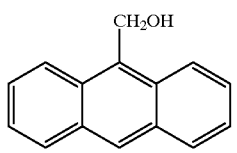

9-anthracenemethanol
Chemical Formula 2

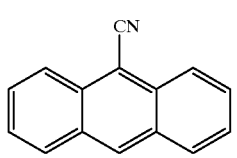

9-anthracenecarbonitrile
Chemical Formula 3

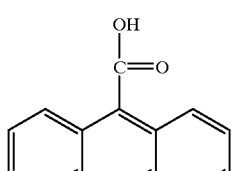

9-anthracenecarboxylic acid
Chemical Formula 4

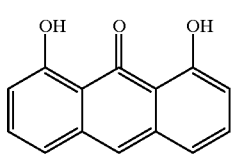

dithranol
Chemical Formula 5

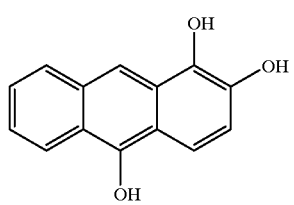

1,2,10-anthracenetriol
Chemical Formula 6

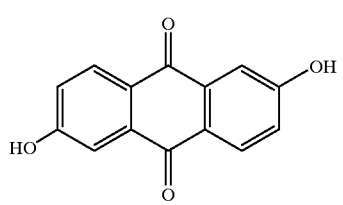

anthraflavic acid
Chemical Formula 7

TABLE 1-continued

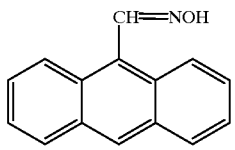

9-anthraldehyde oxime
Chemical Formula 8

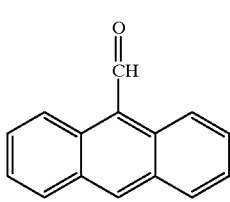

9-anthraldehyde

Chemical Formula 9

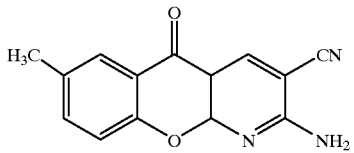

2-amino-7-methyl-5-oxo-5H-
[1]benzopyranol[2,3-b]
pyridine-3-carbonitrile

Chemical Formula 10

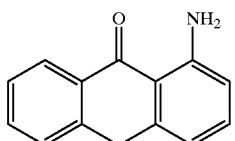

1-aminoanthraquinone
Chemical Formula 11

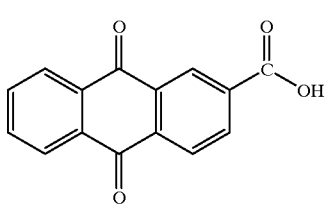

anthraquinone-2-carboxylic acid
Chemical Formula 12

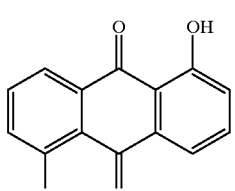

1,5-dihydroxyanthraquinone
Chemical Formula 13

TABLE 1-continued

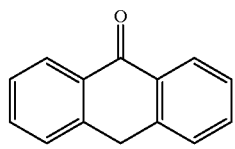

anthrone
Chemical Formula 14

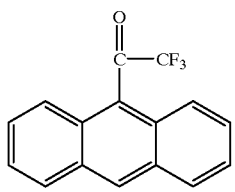

9-anthryl trifluoromethyl ketone
Chemical Formula 15

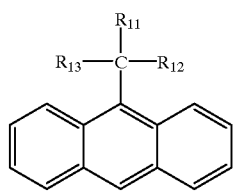

9-alkyl anthracene derivatives
Chemical Formula 16

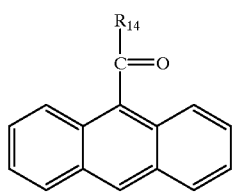

9-carboxyl anthracene derivatives
Chemical Formula 17

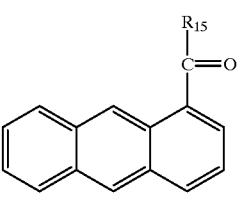

1-carboxyl anthracene derivatives
Chemical Formula 18 wherein $R_{11}$, $R_{12}$, $R_{13}$, $R_{14}$ and $R_{15}$ independently represent hydrogen, hydroxy, hydroxymethyl, or substituted or unsubstituted linear or branched $C_1$–$C_5$ alkyl, alkane, alkoxyalkyl or alkoxyalkane.

36. A method for preparing an anti-reflective coating useful in fabricating semiconductor devices which comprises filtering a solution of a polymer of claim 1 in a solvent, coating said solution on a wafer, and subjecting the coated wafer to hard-baking.

37. A method as set forth in claim 36, wherein the organic solvent is used at an amount of 200–5,000% by weight based on the weight of the polymer and the hard-baking process is carried out at 100–300° C.

38. A method for preparing an anti-reflective coating useful in fabricating semiconductor devices which comprises filtering a solution of a polymer of claim 19 in a solvent, coating said solution on a wafer, and subjecting the coated wafer to hard baking.

39. A method as set forth in claim 38, wherein the organic solvent is used at an amount of 200–5,000% by weight based on the weight of the polymer and the hard-baking process is carried out at 100–300° C.

40. A method for preparing an anti-reflective coating useful in fabricating semiconductor devices which comprises dissolving a polymer of claim 1 or 19 in a solvent to obtain a solution of said polymer, adding to said polymer solution at least one additive selected from the group consisting of the compounds in the following Table 1 to form an anti-reflective coating composition, filtering said composition, coating said composition on a wafer and subjected said wafer to hard baking:

TABLE 1

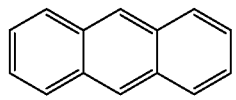

anthracene
Chemical Formula 1

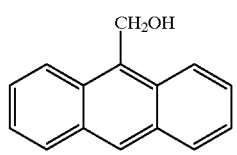

9-anthracenemethanol
Chemical Formula 2

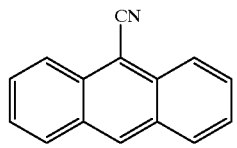

9-anthracenecarbonitrile
Chemical Formula 3

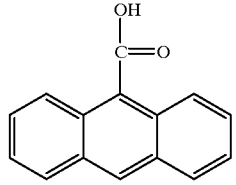

9-anthracenecarboxylic acid
Chemical Formula 4

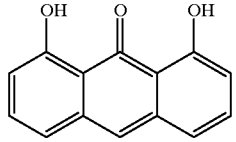

dithranol
Chemical Formula 5

TABLE 1-continued

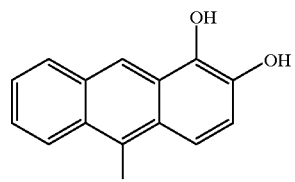

1,2,10-anthracenetriol

Chemical Formula 6

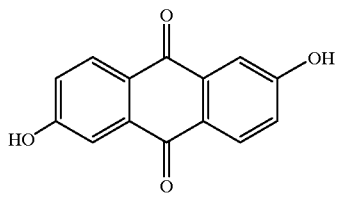

anthraflavic acid

Chemical Formula 7

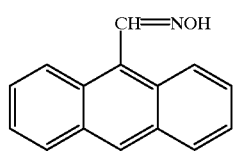

9-anthraldehyde oxime

Chemical Formula 8

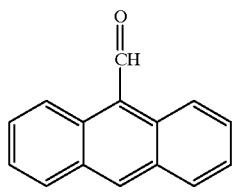

9-anthraldehyde

Chemical Formula 9

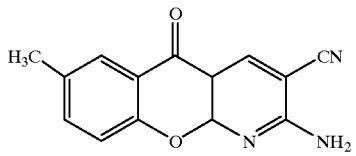

2-amino-7-methyl-5-oxo-5H-
[1]benzopyranol[2,3-b]
pyridine-3-carbonitrile

Chemical Formula 10

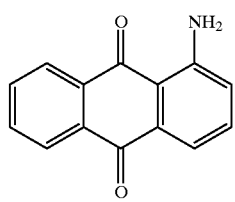

1-aminoanthraquinone

Chemical Formula 11

TABLE 1-continued

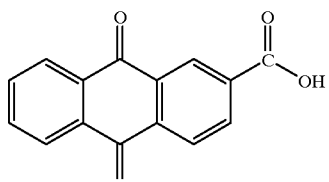

anthraquinone-2-carboxylic acid

Chemical Formula 12

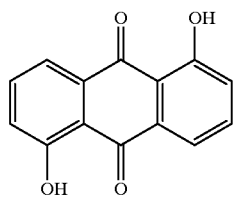

1,5-dihydroxyanthraquinone

Chemical Formula 13

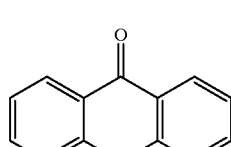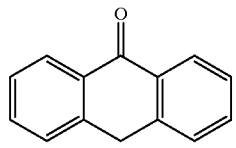

anthrone

Chemical Formula 14

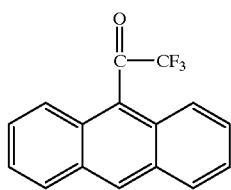

9-anthryl trifluoromethyl ketone

Chemical Formula 15

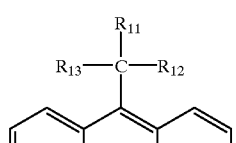

9-alkyl anthracene derivatives

Chemical Formula 16

9-carboxyl anthracene derivatives

Chemical Formula 17

TABLE 1-continued

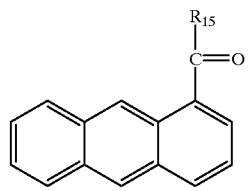

1-carboxyl anthracene derivatives
Chemical Formula 18 wherein $R_{11}$, $R_{12}$, $R_{13}$, $R_{14}$ and $R_{15}$ independently represent hydrogen, hydroxy, hydroxymethyl, or substituted or unsubstituted linear or branched $C_1$–$C_5$ alkyl, alkane, alkoxyalkyl or alkoxyalkane.

41. A method as set forth in claim 40, wherein the organic solvent is used at an amount of 200–5,000% by weight based on the weight of the polymer and the hard-baking process is carried out at 100–300° C.

42. A method as set forth in claim 36 or 38 wherein the organic solvent is selected from the group consisting of methyl 3-methoxy propionate, and cyclohexanone, propyleneglycol methyletheracetate.

43. A method as set forth in claim 40 wherein the additive is used at an amount of 0.1 to 30% by weight.

44. A semiconductor device fabricated by using an antireflective coating of claim 33 or 34.

* * * * *

UNITED STATES PATENT AND TRADEMARK OFFICE
CERTIFICATE OF CORRECTION

PATENT NO.    : 6,309,790 B1  
DATED         : October 30, 2001  
INVENTOR(S)   : Min-Ho Jung, Sung-Eun and Ki-Ho Baik It is certified that error appears in the above-identified patent and that said Letters Patent is hereby corrected as shown below:

Title page,
Item [57], ABSTRACT,
Please replace general formula I with the following formula:
--

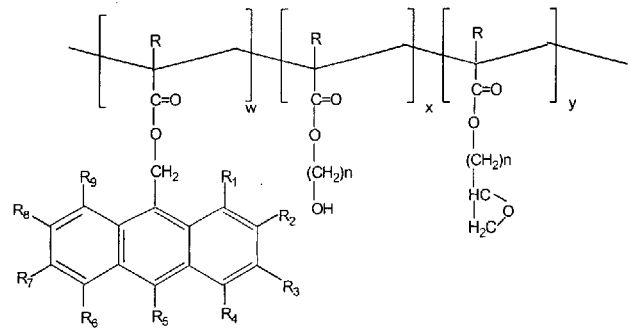

--.

Column 3,
Lines 20-40, please replace general formula I with the following formula:

--

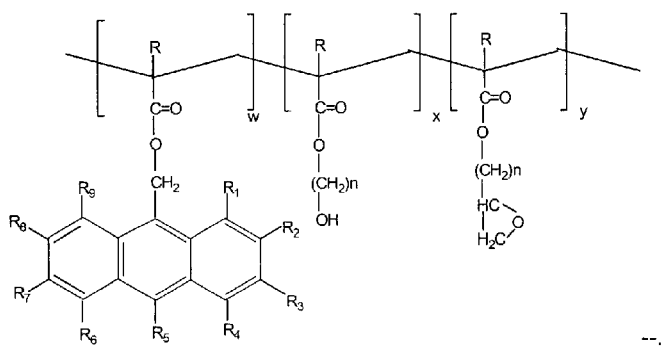

--.

UNITED STATES PATENT AND TRADEMARK OFFICE
CERTIFICATE OF CORRECTION

PATENT NO.    : 6,309,790 B1
DATED         : October 30, 2001
INVENTOR(S)   : Min-Ho Jung, Sung-Eun and Ki-Ho Baik It is certified that error appears in the above-identified patent and that said Letters Patent is hereby corrected as shown below:

Column 16,
Lines 1-19, please replace general formula I with the following formula:

--
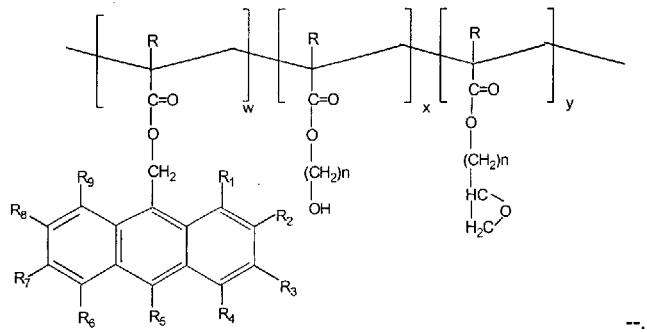
--.

Signed and Sealed this

Twenty-third Day of March, 2004

JON W. DUDAS
*Acting Director of the United States Patent and Trademark Office*